United States Patent
Dakka et al.

(10) Patent No.: US 10,421,698 B2
(45) Date of Patent: Sep. 24, 2019

(54) PRODUCTION OF HIGH OCTANE HYDROCARBON FROM LIGHT ALKANE FEED USING OXIDATION AND ACID CATALYSIS CHEMISTRY

(71) Applicant: ExxonMobil Research and Engineering Company, Annandale, NJ (US)

(72) Inventors: Jihad M. Dakka, Whitehouse Station, NJ (US); Matthew S. Ide, Doylestown, PA (US); David B. Spry, Lebanon, NJ (US); Sumod Kalakkunnath, The Woodlands, TX (US); Guang Cao, Princeton, NJ (US); Patrick L. Hanks, Bridgewater, NJ (US); Cynthia F. Omilian, Whitehouse Station, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 15/839,937

(22) Filed: Dec. 13, 2017

(65) Prior Publication Data

US 2018/0162787 A1     Jun. 14, 2018

Related U.S. Application Data

(60) Provisional application No. 62/433,833, filed on Dec. 14, 2016.

(51) Int. Cl.
C07C 2/86     (2006.01)
C07C 2/02     (2006.01)
(Continued)

(52) U.S. Cl.
CPC ........... *C07C 2/864* (2013.01); *B01J 29/7038* (2013.01); *B01J 29/80* (2013.01); *C07C 1/24* (2013.01);
(Continued)

(58) Field of Classification Search
CPC .. C07C 2/86; C07C 2/62; C07C 31/12; C07C 31/125; C07C 29/50
See application file for complete search history.

(56) References Cited

U.S. PATENT DOCUMENTS 3,644,565 A    9/1968   Biale
3,810,955 A *   5/1974   Sobel ....................... C07C 2/62
                                                           585/300

(Continued)

FOREIGN PATENT DOCUMENTS

EP        0293032 A1    11/1988
EP        0710622 A1     5/1998
WO      9745383 A1    12/1997

OTHER PUBLICATIONS

Hajimirzaee (Preparation, modification and characterization of selective zeolite based catalysts for petrochemical applications, Apr. 2015, University of Birmingham). (Year: 2015).*

(Continued)

*Primary Examiner* — Youngsul Jeong
(74) *Attorney, Agent, or Firm* — Andrew T. Ward; Priya G. Prasad

(57) ABSTRACT

Systems and methods are provided for production of high octane hydrocarbon from an isoparaffin feed using oxidation acid catalysis chemistry.

16 Claims, 3 Drawing Sheets

(51) Int. Cl.

| | |
|---|---|
| *C07C 1/24* | (2006.01) |
| *C07C 2/12* | (2006.01) |
| *C07C 2/62* | (2006.01) |
| *C07C 31/12* | (2006.01) |
| *C07C 31/125* | (2006.01) |
| *C07C 29/50* | (2006.01) |
| *B01J 29/70* | (2006.01) |
| *C07C 5/02* | (2006.01) |
| *C07C 29/132* | (2006.01) |
| *C07C 5/03* | (2006.01) |
| *C07C 5/27* | (2006.01) |
| *C07C 407/00* | (2006.01) |
| *C10G 45/58* | (2006.01) |
| *C10G 50/00* | (2006.01) |
| *C10G 69/12* | (2006.01) |
| *C10G 3/00* | (2006.01) |
| *B01J 29/80* | (2006.01) |
| *B01J 29/50* | (2006.01) |

(52) U.S. Cl.
CPC .............. *C07C 2/12* (2013.01); *C07C 2/62* (2013.01); *C07C 5/02* (2013.01); *C07C 5/03* (2013.01); *C07C 5/2702* (2013.01); *C07C 29/132* (2013.01); *C07C 29/50* (2013.01); *C07C 31/12* (2013.01); *C07C 31/125* (2013.01); *C07C 407/00* (2013.01); *C10G 3/49* (2013.01); *C10G 45/58* (2013.01); *C10G 50/00* (2013.01); *C10G 69/126* (2013.01); *B01J 29/50* (2013.01); *C07C 2523/28* (2013.01); *C07C 2523/34* (2013.01); *C07C 2523/889* (2013.01); *C07C 2529/70* (2013.01); *C10G 2300/104* (2013.01); *C10G 2300/1044* (2013.01); *C10G 2300/1081* (2013.01); *C10G 2300/305* (2013.01); *C10G 2400/02* (2013.01)

(56) References Cited

U.S. PATENT DOCUMENTS

| | | |
|---|---|---|
| 4,384,161 A | 5/1983 | Huang |
| 4,439,409 A | 3/1984 | Puppe et al. |
| 4,826,667 A | 5/1989 | Zones et al. |
| 4,954,325 A | 9/1990 | Rubin et al. |
| 5,236,575 A | 8/1993 | Bennett et al. |
| 5,243,084 A | 9/1993 | Cochran et al. |
| 5,250,277 A | 10/1993 | Kresge et al. |
| 5,254,518 A | 10/1993 | Soled et al. |
| 5,304,698 A | 4/1994 | Husain |
| 5,340,562 A | 8/1994 | O'Young et al. |
| 5,362,697 A | 11/1994 | Fung et al. |
| 5,382,731 A | 1/1995 | Chang et al. |
| 5,414,145 A | 5/1995 | Sheu et al. |
| 5,510,309 A | 4/1996 | Chang et al. |
| 5,523,509 A | 6/1996 | O'Young et al. |
| 5,719,097 A | 2/1998 | Chang et al. |
| 6,077,498 A | 6/2000 | Diaz et al. |
| 6,231,751 B1 | 5/2001 | Canos et al. |
| 6,376,731 B1 | 4/2002 | Evans et al. |
| 6,756,030 B1 | 6/2004 | Rohde et al. |
| 7,713,513 B2 | 5/2010 | Jan et al. |
| 7,842,277 B2 | 11/2010 | Wieslaw et al. |
| 7,982,084 B1 | 7/2011 | Moscoso et al. |
| 8,704,023 B2 | 4/2014 | Wieslaw et al. |
| 8,704,025 B2 | 4/2014 | Wieslaw et al. |
| 2016/0168048 A1* | 6/2016 | Wang ................ C10L 1/04 585/310 |
| 2018/0162786 A1 | 6/2018 | Dakka et al. |
| 2018/0162787 A1 | 6/2018 | Dakka et al. |
| 2018/0162788 A1 | 6/2018 | Dakka et al. |
| 2018/0162789 A1 | 6/2018 | Liu et al. |

OTHER PUBLICATIONS

Albright et al., "Alkylation of isobutane with C4 olefins 1. First-step reactions using sulfuric acid catalyst", Ind. Eng. Chem. Res., 1988, vol. 27, pp. 381-386.

Corma et al., "Chemistry, Catalysts, and Processes for Isoparaffin-Olefin Alkylation: Actual Situation and Future Trends", Cat. Rev. Sc. Eng., 1993, vol. 35, pp. 483-570.

Feng et al., "Catalytic decomposition of tert-butyl hydroperoxide into tert-butyl alcohol over Me-OMS-1s molecular sieves", J. Chem. Ind. Eng., 2015, vol. 66, pp. 3965-3970.

Hutson, "Phillips HF Alkylation Process for Alkylation of C3, C4, C5 Olefins", Handbook of Petroleum Refining Processes, R.A. Meyers., Ed.

Lin et al., "Decomposition of tert-butyl hydroperoxide into tert butyl alcohol and O2 catalyzed by bimessite-type manganese oxides: Kinetics and activity", Cat. Comm., 2014, vol. 49, pp. 6-9.

Liu et al., "Catalytic Partial Oxidation of Cyclohexane by Bimetallic Ag/Pd Nanoparticles on Magnesium Oxide", Chem. Eur. J.

Luo et al., "One-pot synthesis of MWW zeolite nanosheets using a rationally designed organic structure-directing agent", Chem. Sci., 2015, vol. 6, pp. 6320-6324.

O'Young, "Hydrothermal Synthesis of Manganese Oxides with Tunnel Structures", in Expanded Clays and Other Microporous Structures, vol. II, 333, M.L. Occelli, H.E. Robson Eds. Van Nostrand Reinhold, NY, 1992.

Shah, "UOP HF Alkylation Process", Handbook of Petroleum Refining Processes, R.A. Meyers, Ed., 1986, pp. XX-XX.

The International Search Report and Written Opinion of PCT/US2017/065954 dated Dec. 13, 2017.

The International Search Report and Written Opinion of PCT/US2017/065955 dated Dec. 13, 2017.

The International Search Report and Written Opinion of PCT/US2017/065958 dated Dec. 13, 2017.

The International Search Report and Written Opinion of PCT/US2017/065960 dated Dec. 13, 2017.

\* cited by examiner

PRODUCTION OF HIGH OCTANE HYDROCARBON FROM LIGHT ALKANE FEED USING OXIDATION AND ACID CATALYSIS CHEMISTRY

CROSS-REFERENCE TO RELATED APPLICATIONS

This application claims the benefit of provisional U.S. Ser. No. 62/433,833, filed Dec. 14, 2016, the entire contents of which are expressly incorporated by reference herein. This application is also related to several other co-pending U.S. applications, filed on even date herewith and bearing U.S. patent application Ser. Nos. 15/839,959 and 15/839,974.

FIELD

Systems and methods are provided for production of high octane hydrocarbon from an isoparaffin feed using oxidation acid catalysis chemistry.

BACKGROUND

In conventional petroleum processes, alkylate is typically used to describe a product formed by an alkaylation process involving an isoparaffin-containing feed and an olefin-containing feed. Industrially, alkylation reactions often correspond to the reaction of a $C_2$ to $C_5$ olefin, normally 2-butene, with isobutane in the presence of an acidic catalyst to produce a so-called alkylate. This alkylate is a valuable blending component in the manufacture of gasoline due not only to its high octane rating but also to its sensitivity to octane-enhancing additives. Industrial isoparaffin-olefin alkylation processes have historically used hydrofluoric or sulfuric acid catalysts under relatively low temperature conditions. The sulfuric acid alkylation reaction is particularly sensitive to temperature, with low temperatures being favored to minimize the side reaction of olefin polymerization. Acid strength in these liquid acid catalyzed alkylation processes is typically maintained at 88 to 94 weight percent by the continuous addition of fresh acid and the continuous withdrawal of spent acid. The hydrofluoric acid process is less temperature sensitive and the acid is more easily recovered and purified. A general discussion of sulfuric acid alkylation can be found in a series of three articles by L. F. Albright et al., "Alkylation of Isobutane with $C_4$ Olefins", 27 Ind. Eng. Chem. Res., 381-397, (1988). For a survey of hydrofluoric acid catalyzed alkylation, see 1 Handbook of Petroleum Refining Processes 23-28 (R. A. Meyers, ed., 1986). An overview of the entire technology can be found in "Chemistry, Catalysts and Processes of Isoparaffin-Olefin Alkylation—Actual Situation and Future Trends, Corma et al., Catal. Rev.—Sci. Eng. 35(4), 483-570 (1993).

Both sulfuric acid and hydrofluoric acid alkylation share inherent drawbacks including environmental and safety concerns, acid consumption, and sludge disposal. Research efforts have, therefore, been directed to developing alkylation catalysts which are equally as effective as, or more effective than, sulfuric or hydrofluoric acids but which avoid many of the problems associated with these two acids.

U.S. Pat. No. 3,644,565 discloses alkylation of a paraffin with an olefin in the presence of a catalyst comprising a Group VIII noble metal present on a crystalline aluminosilicate zeolite having pores of substantially uniform diameter from about 4 to 18 angstrom units and a silica to alumina ratio of 2.5 to 10, such as zeolite Y. The catalyst is pretreated with hydrogen to promote selectivity.

U.S. Pat. No. 4,384,161 describes a process of alkylating isoparaffins with olefins to provide alkylate using a large-pore zeolite catalyst capable of absorbing 2,2,4-trimethylpentane, for example, ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The addition of a Lewis acid is reported to increase the activity and selectivity of the zeolite, thereby effecting alkylation with high olefin space velocity and low isoparaffin/olefin ratio.

U.S. Pat. No. 5,304,698 describes a process for the catalytic alkylation of an olefin with an isoparaffin comprising contacting an olefin-containing feed with an isoparaffin-containing feed with a crystalline microporous material selected from the group consisting of MCM-22, MCM-36, and MCM-49 under alkylation conversion conditions of temperature at least equal to the critical temperature of the principal isoparaffin component of the feed and pressure at least equal to the critical pressure of the principal isoparaffin component of the feed.

An additional difficulty with alkylation processes can be related to the availability and/or cost of the feeds for forming alkylate. Light paraffin feeds, such as a feed containing isobutane, are generally considered low cost feeds. However, the corresponding olefin feed for forming alkylate can generally be of higher cost, particularly when the corresponding olefin feed corresponds to a $C_{3+}$ olefin feed, such as a feed of butene or isobutene, because these olefins are typically produced via dehydrogenation reaction which is a high temperature, thermodynamically limited process.

U.S. Pat. No. 5,243,084 describes a process for oxidation of isobutane to tertiary butyl hydroperoxide and tertiary butyl alcohol.

U.S. Patent Application No. 62/433,833 filed on Dec. 14, 2016 describes a process of selectively oxidizing an isoparaffin feed to an alcohol, such as isobutane to t-butyl alcohol, and then converting the alcohol to an alkene. A solid acid catalyst can facilitate conversion of tertiary alcohols to alkene under alkylation conditions. The solid acid catalyst can then facilitate alkylation of isoparaffin using the in-situ formed alkenes in the presence of the in-situ formed water.

SUMMARY

Systems and methods are provided for production of high octane hydrocarbon from an isoparaffin feed using oxidation acid catalysis chemistry. In one aspect a method for producing a high octane hydrocarbon is provided, the method comprising, oxidizing an isobutane containing feed in the presence of oxygen to form an oxidation effluent comprising tert-butyl alcohol ("TBA") and an oxygenate impurity, such as water, methanol, acetone, or a combination thereof, at least 0.5 wt % of the isobutane in the isobutane containing feed being converted under the oxidation conditions; exposing at least a portion of the oxidation effluent to a solid acid catalyst, wherein the solid acid catalyst comprises a crystalline microporous material of the MWW framework type, under dehydration conditions to form a dehydration effluent comprising $C_4$ hydrocarbons; at least 80% of the TBA being converted under the dehydration conditions; exposing at least a portion of the dehydration effluent to a second solid acid catalyst, wherein the second solid acid catalyst comprises a crystalline microporous material of the MWW framework type, under dimerization conditions to form a dimerization effluent comprising $C_8$ hydrocarbons, wherein at least 90% of the $C_8$ hydrocarbons in the dimerization effluent are $C_8$ olefins. The method may further include hydrogenating the $C_8$ olefins to form $C_8$.

It is contemplated that the isobutane containing feed can be produced via isomerization of an n-butane containing feed over a bifunctional catalyst. In certain aspects, the method further includes recycling a portion of unconverted n-butane, unconverted isobutane, or a combination of unconverted n-butane and unconverted isobutane to the n-butane containing feed for re-entry to the isomerization reactor. This recycling may occur before or after hydrogenating the $C_8$ olefins. In yet another aspect, the recycling occurs after the oxidizing and before exposing at least a portion of the oxidation effluent to a solid acid catalyst under dehydration conditions.

In another aspect, the crystalline microporous material of the MWW framework type of either the first or second solid acid catalyst is selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and mixtures thereof. In still another aspect, solid acid catalyst(s) comprise a mixed metal oxide based on oxides of Fe/W/Zr, W/Zr, Ce/W/Zr, Cu/W/Zr, Mn/W/Zr, or a combination thereof. The solid acid catalyst(s) may further comprise an inorganic oxide binder. The solid acid catalyst and the second solid acid catalyst may be the same or different and may be located in the same or different reactor vessel(s).

In another aspect dimerization conditions can include a dimerization temperature of about 100° C. to about 210° C., e.g. about 150° C. to about 190° C., and a dimerization pressure of about 15 psig to about 1000 psig. In yet another aspect, the $C_8$ hydrocarbon portion of the dimerization effluent has an octane rating, as determined by (RON+MON)/2, of at least 95, e.g. at least 98 or at least 100.

Also provided herein is a system for the production of high octane hydrocarbon comprising: an oxidation reactor comprising an isoparaffin feed inlet and an oxidation reactor outlet; a dehydration reactor comprising a dehydration reactor inlet, a dehydration reactor outlet, and a solid acid catalyst comprising a zeolite, a mixed metal oxide, a crystalline microporous material of the MWW framework type, or a combination thereof, the dehydration reactor inlet being in fluid communication with the oxidation reactor outlet; a dimerization reactor comprising a dimerization reactor inlet, a dimerization reactor outlet, and a solid acid catalyst comprising a zeolite, a mixed metal oxide, a crystalline microporous material of the MWW framework type, or a combination thereof, the dimerization reactor inlet being in fluid communication with the dehydration reactor outlet; and a hydroprocessing reactor comprising a hydroprocessing reactor inlet, a hydroprocessing reactor outlet, and a hydroprocessing catalyst, the hydroprocessing reactor inlet being in fluid communication with the dimerization reactor outlet. In certain embodiments, the system further includes an isomerization reactor with an n-paraffin stream inlet and an isoparaffin feed outlet, wherein the isoparaffin feed outlet of the isomerization reactor is in fluid communication with the isoparaffin feed inlet of the oxidation reactor.

In another aspect, the system further comprises further comprising a recycle line providing fluid communication between the dimerization reactor outlet and the isoparaffin feed inlet. In yet another aspect, the system further comprises a distillation vessel interposed between the oxidation reactor and the dehydration reactor; and a recycle line providing fluid communication between the distillation vessel and the isoparaffin feed inlet In certain aspects, the dehydration reactor, the dimerization reactor, and the hydroprocessing reactor are contained within a single vessel. In other aspects, a combination of two of the three reactors are in the same vessel with the other in a different vessel. In another aspect, all three reactors are in separate vessels.

DETAILED DESCRIPTION

Overview

In various aspects, systems and methods are provided for forming alkylate from an isoparaffin-containing feed. Instead of using an olefin co-feed to form alkylate, olefins for the alkylation reaction can be generated in-situ from a portion of the isoparaffin-containing feed. This can be achieved, for example, by using selective oxidation to convert a portion of isoparaffins into alcohol, such as conversion of isobutane to t-butyl alcohol. The alcohol can then be converted to an alkene, such as conversion of t-butyl alcohol to isobutene, in the alkylation reaction environment. It has been unexpectedly discovered that a solid acid catalyst can facilitate conversion of tertiary alcohols to alkene under alkylation conditions. A solid acid catalyst can then facilitate dimerization of the in-situ formed isobutene in the presence of the in-situ formed water to isooctene. The isooctene can then easily be hydrogenated to isooctane. This conversion of alcohol to alkene, and then alkene dimerization, can occur in part due to the ability of a solid acid catalyst to tolerate water. Moreover and surprisingly, the presence of water combined with the appropriate reaction temperature promotes dimerization of the alkene, but suppresses further polymerizations. A catalyst having an MWW framework is an example of a suitable solid acid catalyst.

Figure 1:
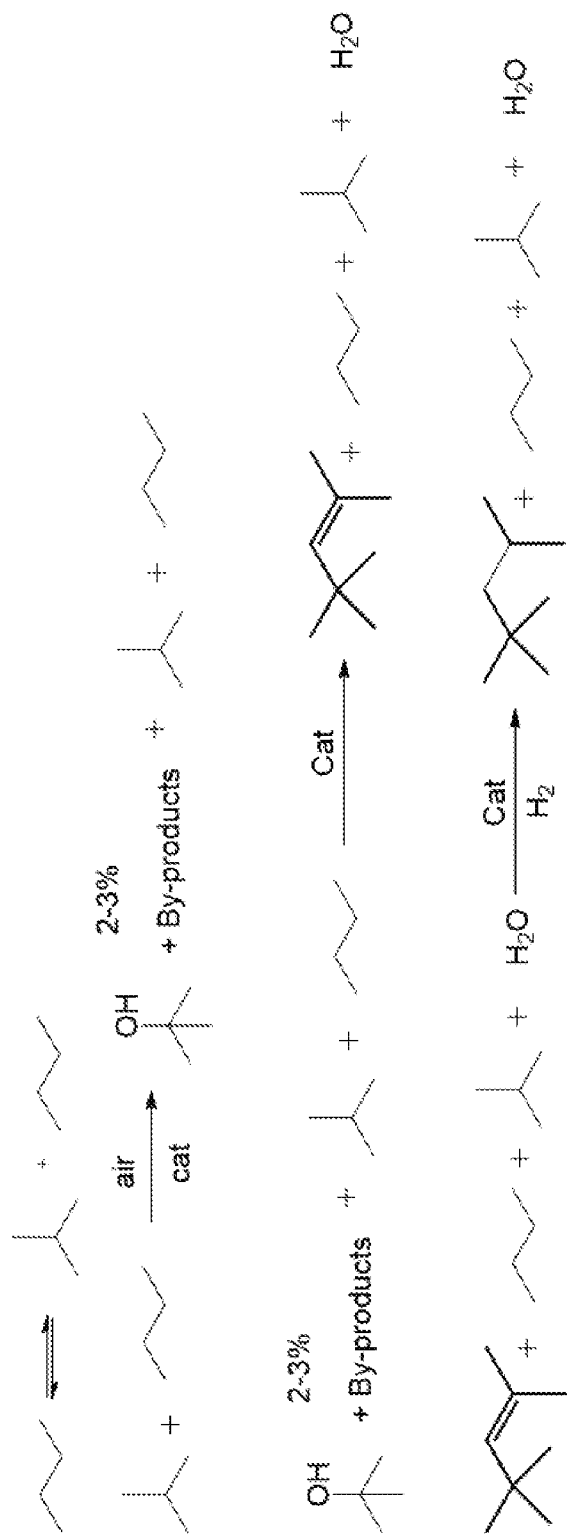
FIG. 1 show an example of a reaction scheme for forming alkylate from isoparaffins via oxidation of a portion of the isoparaffins to form alcohols.

FIG. 1 shows an example of the overall reaction scheme that can be used to form alkylate from an n-paraffin feed. In a first reactor and/or reaction stage, an n-paraffin feed (or a portion of such a feed) can be exposed to isomerization conditions to form an iso-paraffin feed comprising isoparaffins and unreacted n-paraffins. In FIG. 1, the n-paraffin feed is represented by n-butane. In a second reactor and/or reaction stage, the isoparaffin feed (or a portion of such feed) can be exposed to selective oxidation conditions. The selective oxidation conditions can result in only partial conversion of the feed, so that the resulting products include a substantial portion of unreacted isoparaffin, n-paraffins, and other byproducts such as oxygenates. In addition to unreacted isoparaffin, the selective oxidation conditions can form t-butyl alcohol ("TBA") and various additional side products, such as water, methanol, and acetone. This mixture from selective oxidation step has been found to be an effective feed, without separation, for produce an alkylation. In a third reactor and/or reaction stage, a mixture of unreacted isoparaffin, n-paraffin, and alcohol (and optionally at least a portion of the additional side products) can be exposed to a solid acid catalyst under controlled dehydration/dimerization conditions. Some examples of solid acid catalysts include zeolitic catalysts, such as catalysts having an MWW framework type. An MWW framework catalyst corresponds to a catalyst including a crystalline microporous material of the MWW framework type. The solid acid catalyst can convert the TBA to isobutene at nearly 100% conversion, and then dimerize the isobutene, resulting in the formation of isooctene, such as the 2,4,4-trimethyl-2-pentene shown in FIG. 1. The resulting isooctane can be easily hydrogenated to isooctane, such 2,4,4-trimethylpentane shown in FIG. 1. Because alkylation reactions are typically performed with an excess of isoparaffin to reduce or minimize olefin oligomerization reactions, the remaining unreacted isoparaffin from the alkylation reaction (and/or from the oxidation reaction) can be recycled for further passes through the reaction process train. The net result can be the upgrading of a low value isobutane stream to high octane blending component for gasoline.

A common method for characterizing the octane rating of a composition is to use an average of the Research Octane Number (RON) and the Motor Octane Number (MON) for a composition. This type of octane rating can be used to determine the likelihood of "knocking" behavior when operating a conventional spark ignition engine. In this discussion, octane rating is defined as (RON+MON)/2, where RON is research octane number and MON is motor octane number. Although various methods are available for determining RON and MON, in the claims below, references to Research Octane Number (RON) correspond to RON determined according to ASTM D2699, while references to Motor Octane Number (MON) correspond to MON determined according to ASTM D2700.

In this discussion, the naphtha boiling range is defined as about 50° F. (~10° C., roughly corresponding to the lowest boiling point of a pentane isomer) to 350° F. (~177° C.). It is noted that due to practical consideration during fractionation (or other boiling point based separation) of hydrocarbon-like fractions, a fuel fraction formed according to the methods described herein may have a T5 or a T95 distillation point corresponding to the above values, as opposed to having initial/final boiling points corresponding to the above values. Compounds ($C_{4-}$) with a boiling point below the naphtha boiling range can be referred to as light ends. Optionally, a naphtha boiling range fuel composition can have a higher T5 distillation point, such as a T5 distillation point of at least about 15° C., or at least about 20° C., or at least about 30° C. In particular, a naphtha boiling range fuel composition can have a T5 to T95 distillation point range corresponding to a T5 of at least about 10° C. and a T95 of about 177° C. or less; or a T5 of at least about 15° C. and a T95 of about 177° C. or less. In the claims below, ASTM D86 should be used for determining boiling points (including fractional weight boiling points). Compounds with boiling points above 177° C. can correspond to distillate fuel boiling range compounds.

Solid acid catalysts can generally refer to solid materials that can provide acidic sites for catalysis of reactions. Some examples of solid acid catalysts can include various types of zeolites and/or molecular sieves. For example, in zeolitic structures that include silicon and aluminum in the framework, the aluminum atoms can potentially serve as acidic catalysis sites. Suitable zeolitic materials for use as solid acid catalysts can include ZSM-4, ZSM-20, ZSM-3, ZSM-18, zeolite Beta, faujasite, mordenite, zeolite Y and the rare earth metal-containing forms thereof. More generally, crystalline materials having a porous framework structure built from tetrahedra atoms connected by bridging oxygen atoms can potentially be suitable solid acid catalysts. This can include aluminosilicates having a zeolitic framework as well as crystalline structures containing oxides of heteroatoms different from silicon and aluminum. Such heteroatoms can include any heteroatom generally known to be suitable for inclusion in a zeolitic framework, such as gallium, boron, germanium, phosphorus, zinc, and/or other transition metals that can substitute for silicon and/or aluminum in a zeolitic framework Still other examples of solid acid catalysts can include mixed metal oxides. Examples of suitable mixed metal oxides can include mixed metal oxides based on oxides of Fe/W/Zr, W/Zr, Ce/W/Zr, Cu/W/Zr, and/or Mn/W/Zr.

As used herein, the term "crystalline microporous material of the MWW framework type" includes one or more of: a) Molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, which is incorporated by reference with respect to definitions for unit cells, building blocks, and crystal structures); b) Molecular sieves made from a common second degree building block, being a 2-dimensional tiling of such MWW framework topology unit cells, forming a monolayer of one unit cell thickness, preferably one c-unit cell thickness; c) Molecular sieves made from common second degree building blocks, being layers of one or more than one unit cell thickness, wherein the layer of more than one unit cell thickness is made from stacking, packing, or binding at least two monolayers of MWW framework topology unit cells. The stacking of such second degree building blocks can be in a regular fashion, an irregular fashion, a random fashion, or any combination thereof; and d) molecular sieves made by any regular or random 2-dimensional or 3-dimensional combination of unit cells having the MWW framework topology.

Crystalline microporous materials of the MWW framework type include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Examples of crystalline microporous materials of the MWW framework type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), UZM-8HS (described in U.S. Pat. No. 7,713,513), UZM-37 (described in U.S. Pat. No. 7,982,084); EMM-10 (described in U.S. Pat. No. 7,842,277), EMM-12

(described in U.S. Pat. No. 8,704,025), EMM-13 (described in U.S. Pat. No. 8,704,023), MIT-1 (described by Luo et al in Chem. Sci., 2015, 6, 6320-6324), and mixtures thereof, with MCM-49 generally being preferred.

In some embodiments, the crystalline microporous material of the MWW framework type employed herein may be an aluminosilicate material having a silica to alumina molar ratio of at least 10, such as at least 10 to less than 50.

In some embodiments, the crystalline microporous material of the MWW framework type employed herein may be contaminated with other crystalline materials, such as ferrierite or quartz. These contaminants may be present in quantities of less than about 10% by weight, normally less than about 5% by weight.

The above molecular sieves may be formed into extrudates with or without another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia, or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide binder may vary widely. For example, the amount of binder employed may be as little as 0 wt %, or alternatively at least 1 wt %, or at least 5 wt %, or at least 10 wt %, whereas in other embodiments the catalyst may include up to 90 wt %, for example up 80 wt %, such as up to 70 wt %, for example up to 60 wt %, such as up to 50 wt % of a binder material.

In an aspect, a solid acid catalyst can be substantially free of any binder containing amorphous alumina. As used herein, the term "substantially free of any binder containing amorphous alumina" means that the solid acid catalyst used herein contains less than 5 wt %, such as less than 1 wt %, and preferably no measurable amount, of amorphous alumina as a binder. Surprisingly, it is found that when the solid acid catalyst is substantially free of any binder containing amorphous alumina, the activity of the catalyst for isoparaffin-olefin alkylation can be significantly increased, for example by at least 50%, such as at least 75%, even at least 100% as compared with the activity of an identical catalyst but with an amorphous alumina binder.

Isomerization of n-Butane to Form Isobutane

Isomerization of n-butane to form isobutane is a well known industrial process and any convenient method may be used for the isomerization reaction. Representative n-paraffin isomerization processes are described in U.S. Pat. Nos. 5,719,097, 5,510,309, and 5,382,731, which are incorporated by reference. In a typical case, isomerization may take place at effective isomerization conditions in a reactor employing an isomerization catalyst. The isomerization catalyst can comprise a refractory metal oxide support base (e.g., alumina, silica-alumina, zirconia, titanium, etc.) on which is deposited a catalytically active metal selected from the group consisting of Group VIB, Group VIIB, Group VIII metals and mixtures thereof, preferably Group VIII metals, more preferably noble Group VIII metals, most preferably platinum or palladium and optionally including a promoter or dopant such as halogen, phosphorus, boron, yttria, magnesia, etc. preferably halogen, yttria or magnesia, most preferably fluorine. The catalytically active metals are present in the range of from about 0.1 to about 5.0 wt. %, preferably from about 0.1 to about 2.0 wt. %. The promoters and dopants are used to control the acidity of the isomerization catalyst. Thus, when the isomerization catalyst employs a base material such as alumina, acidity is imparted to the resultant catalyst by addition of a halogen, preferably fluorine. When a halogen is used, preferably fluorine, it is present in an amount in the range of about 0.1 to about 10 wt. %, preferably about 0.1 to about 3 wt. %, more preferably from about 0.1 to about 2 wt. % most preferably from about 0.5 to about 1.5 wt. %. Similarly, if silica-alumina is used as the base material, acidity can be controlled by adjusting the ratio of silica to alumina or by adding a dopant such as yttria or magnesia which reduces the acidity of the silica-alumina base material as taught in U.S. Pat. No. 5,254,518 (Soled, McVicker, Gates, Miseo)

Any suitable isomerization conditions can be employed in the process of the present disclosure. Generally, an n-butane and hydrogen, preferably hydrogen gas, are premixed to provide an isomerization feed stream which is then charged to an isomerization zone, which can be defined by a reactor vessel, and contacted with the catalyst contained therein at a reaction temperature of at least about 80° F. Preferably the reaction temperature is in the range of from about 100° F. to about 600° F., more preferably the reaction temperature is in the range of from about 120° F. to about 575° F., and, most preferably, the reaction temperature is in the range from 140° F. to 550° F.

The reaction pressure can be in the range of from below atmospheric pressure upwardly to about 700 pounds per square inch absolute (psia), preferably, from about atmospheric (i.e., 14.7 psia) to about 600 psia and, most preferably, from 15 psia to 550 psia.

The n-butane can be contacted by any suitable means, method(s), or manner with the catalyst contained within the isomerization zone. The contacting step can be operated as a batch process step or, preferably, as a continuous process step. In the latter operation, a solid catalyst bed, or a moving catalyst bed, or a fluidized catalyst bed can be employed. Any of these operational modes have advantages and disadvantages, and those skilled in the art can select the one most suitable for a particular fluid and catalyst.

The flow rate at which the n-butane is charged to the isomerization zone at a liquid-volume hourly space velocity ("LHSV") in the range of from exceeding 0 hour$^{-1}$ upwardly to about 1000 hour$^{-1}$. The term "liquid-volume hourly space velocity", as used herein, shall mean the numerical ratio of the rate at which feed is charged to a reactor in volume per hour divided by the volume of catalyst contained in the reactor to which the feed is charged. The preferred LHSV of the isomerization feed to the reaction zone can be in the range of from about 0.25 hour$^{-1}$ to about 250 hour$^{-1}$ and, most preferably, in the range from 0.5 hours$^{-1}$ to 100 hours$^{-1}$.

Generally, the hydrogen is charged to the isomerization zone so as to provide a molar ratio of hydrogen to feed hydrocarbon(s), i.e., hydrogen-to-hydrocarbon ($H_2$:HC)

molar ratio, used in the alkane isomerization process of this invention generally in the range of from about 0.01:1 to about 20:1, preferably in the range of from about 0.02:1 to about 5:1, and, most preferably, in the range of from about 0.05:1 to about 3:1.

The isomerization product, i.e., isobutane, can be optionally subjected to any suitable separation means (e.g., fractional distillation) to separate the desired formed product hydrocarbon isomers (e.g., isobutane) from unconverted feed hydrocarbon(s) (e.g., n-butane) and other hydrocarbon(s) which may be present in the product. The desired product hydrocarbon isomer is thus recovered from the effluent.

Oxidation of Isobutane to Form Mixed Feed of Isobutane and t-Butyl Alcohol

Oxidation of isobutane for formation of t-butyl hydroperoxide is a known industrial process. While this oxidation process is often employed for production of peroxides, the process also generates t-butyl alcohol. The amount of alcohol production can vary depending on the conditions and the reaction configuration. For example, U.S. Pat. No. 5,243,084 describes systems and methods for producing t-butyl alcohol as a product from oxidation of isobutane.

In various aspects, oxidation of isobutane (and/or other $C_5$-$C_6$ isoparaffins) to form t-butyl alcohol (and/or other tertiary $C_5$-$C_6$ alcohols) can be performed by any convenient known oxidation method. The isoparaffin-containing feed can correspond to a feed including isobutane, $C_{4+}$ isoparaffins, $C_{5+}$ isoparaffins, $C_4$-$C_5$ isoparaffins, or $C_4$-$C_6$ isoparaffins. In some aspects, the isoparaffin-containing feed can contain at least 80 wt % of isoparaffins (and up to 100 wt %), or at least 90 wt %, or at least 95 wt %, or at least 99 wt %, such as a feed that substantially contains isoparaffins (i.e., 99.5 wt % or higher). In some aspects, the isoparaffin-containing feed can correspond to an isobutane-containing feed that contains at least 80 wt % of isobutane (and up to 100 wt %), or at least 90 wt %, or at least 95 wt %, or at least 99 wt %, such as a feed that substantially contains isobutane (i.e., 99.5 wt % or higher). In various aspects, other components present in the isoparaffin-containing feed (such as an isobutane-containing feed) can include n-paraffins, cycloparaffins, and/or less than about 2 wt % of compounds typically present due to the nature of a process that generated the isoparaffin feed.

As an example, isobutane can be reacted with oxygen in a reactor to produce a mixture of t-butyl hydroperoxide along with t-butyl alcohol. The isobutane oxidation reaction conditions in the oxidation reactor can include, for example, a reaction temperature of about 100° C. to about 200° C., a pressure of about 200 psig (~1.4 MPag) to about 500 psig (~3.4 MPag), and a residence time in the oxidation zone of about 1 hour to about 15 hours. Oxygen can be used as the oxidant, although minor amounts of nitrogen and/or other inert gases can also be present.

The above reaction conditions can generate a weight ratio of t-butyl alcohol to t-butyl hydroperoxide in the liquid phase of about 0.8. Due to the higher vapor pressure of t-butyl alcohol, withdrawing the vapor above the reaction zone can result in a gas phase product with a weight ratio of t-butyl alcohol to t-butyl hydroperoxide of roughly 1.0. This can be facilitated, for example, by operating the oxidation reactor to maintain the reaction mixture at or near the boiling point. The withdrawn vapor can also include, for example, unreacted isobutane and other additional reaction side products. These additional reaction products can include, for example, water and oxygenate impurities, such as methanol and acetone. Depending on the nature of the fractionation, the ratio of t-butyl alcohol to t-butyl hydroperoxide can be further increased. In some aspects, a fraction enriched in t-butyl hydroperoxide can be returned to the oxidation reactor. For a fraction containing t-butyl alcohol, the fraction can optionally be exposed to elevated temperatures of about 100° C. to about 200° C. for additional time to allow for further decomposition of t-butyl hydroperoxide to t-butyl alcohol. Without being bound by any particular theory, it is believed that forming alcohols from isoparaffins by oxidation as described herein can provide a method for alcohol formation under lower severity conditions in comparison with processes such as high temperature reforming. This can allow the conditions for formation of alcohol to be more similar to the eventual conditions for alkylate formation. Additionally or alternately, it is believed that the selectivity of alcohol formation can be improved relative to a high temperature reforming process.

It is noted that other isoparaffins can potentially be oxidized to generate tertiary alcohols. For example, an isopentane or isohexane feed could be oxidized to generated tertiary alcohols. This could be useful, for example, if an available source of isoparaffins includes a mixture of $C_{4+}$ isoparaffins. While use of higher carbon number isoparaffins could lead to formation of compounds during alkylation that are above the traditional naphtha boiling range for gasoline formation, such heavier compounds can be readily separated by boiling point separation and used as part of a distillate fuel fraction.

Another potential difficulty with $C_{5+}$ isoparaffins is that such isoparaffins contain multiple types of carbon sites. Isobutane corresponds to an isoparaffin with three primary (i.e., terminal) carbons and one tertiary carbon. When isobutane is oxidized, the selectivity for forming t-butyl alcohol is high, as the primary carbons have only a limited ability to stabilize the reaction intermediates that could allow for formation of an alcohol. Additionally, once t-butyl alcohol is formed, little or no transfer of the alcohol from the tertiary carbon to a primary carbon would be expected. By contrast, an isopentane (such as 2-methylbutane) includes 3 primary carbons, a tertiary carbon, and a secondary carbon. While the tertiary carbon is the most favorable location for formation of an alcohol, the secondary carbon can also be a suitable location. As a result, oxidation of a $C_{5+}$ isoparaffin can typically result in formation of a mixture of alcohols. Additionally, the presence of multiple non-primary carbons can also facilitate migration of the alcohol group after formation and/or migration of the double bond in the resulting in-situ olefin. As a result, using alcohols formed from $C_{5+}$ paraffins can tend to lead to production of a larger mixture of alkylate products, as opposed to the relatively high selectivity for formation of tri-methylpentanes that is exhibited when isobutane is used as the feed for oxidation. Because tri-methylpentanes can have a relatively high octane value, the formation of a wider variety of products when using $C_{5+}$ isoparaffins can tend to reduce the octane value of the resulting alkylate.

Before being sent to the oxidation reactor and/or the alkylation reactor, the isoparaffin feed and/or the oxidation product fraction containing the tertiary alcohol may be treated to remove catalyst poisons e.g., using guard beds with specific absorbents for reducing the level of S, N, and/or organic acids to values which do not affect catalyst stability activity and selectivity. It is noted that the alkylation process described herein can be conducted in any known reactor, including reactors which allow for continuous or semi-continuous catalyst regeneration, such as fluidized and moving bed reactors, as well as swing bed reactor systems where multiple reactors are oscillated between on-stream mode and regeneration mode. Surprisingly, however, it is found that catalysts employing MWW framework type molecular sieves show unusual stability when used in olefin dimerization. Thus, MWW-containing alkylation catalysts can be suitable for use in simple fixed bed reactors (including trickle-bed reactors), without swing bed capability. In such cases, cycle lengths (on-stream times between successive catalyst regenerations) in excess of 150 days may be obtained.

Formation of Isooctene from t-Butyl Alcohol

In various aspects, a feed of t-butyl alcohol or a mixed feed of isobutane and t-butyl alcohol can be formed based on generation of t-butyl alcohol as described above. In some aspects, the feed can include isobutane and t-butyl alcohol in a molar ratio and/or volume ratio of about 1:1 to about 40:1. In another aspect, the feed does not include any isobutane. Optionally, the feed can also include other oxygenates, such as methanol and/or acetone formed as additional products during oxidation. More generally, the molar ratio and/or volume ratio of isoparaffin to tertiary alcohol in the reactor feed can be from about 2:1 to about 100:1, or about 10:1 to about 75:1, or about 10:1 to about 40:1. Optionally, one or more additional oxygenate products generated during oxidation, such as methanol and/or acetone, may be included as part of the oxidation product fraction containing the t-butyl alcohol. In some aspects, the molar ratio and/or volume ratio of t-butyl alcohol to acetone in an oxidation product fraction (and/or the feed to alkylation) can be about 8:1 to about 200:1, or about 8:1 to about 100:1, or about 10:1 to about 150:1. In some aspects, the molar ratio and/or volume ratio of t-butyl alcohol to methanol in an oxidation product fraction (and/or the feed to alkylation) can be about 8:1 to about 200:1, or about 8:1 to about 100:1, or about 10:1 to about 150:1. At typical alkylation temperatures, the volume ratio of components in an alkylation feed and/or in an alkylation effluent can be similar to the molar ratio.

During the process, the t-butyl alcohol (and/or other tertiary alcohol) can be substantially quantitatively converted to olefin and water under the dehydration conditions in the presence of a solid acid catalyst. The resulting isobutene olefins can then dimerize to form isooctene under dimerization conditions in the presence of the solid acid catalyst. In an alternative embodiment of the process, one may start with isobutene and simply add water to mimic the dehydration of t-butyl alcohol reaction products.

Operating pressure can suitably be from about 15 to about 1500 psig (~104 kPag to ~10.3 MPag), such as about 400 psig (~2.8 MPag) to about 1000 psig (6.9 MPag). In some aspects, the operating temperature can be from about 100° C. to about 210° C., or about 130° C. to about 190° C., or about 150° C. to about 170° C. Without being bound to a particular theory, it is believed that the presence of water in the feed, or the alcohol that dehydrates to form water and an olefin, selectively adsorbs on strong acid sites (often Bronsted acid sites) found in microporous zeolite catalysts. The adsorption of the water on the acid site decreases the acid strength of the acid site, which in turn significantly decreases the capability of the catalyst to enable further polymerizations that require these strong acid sites. The low operating temperature is required because the concentration of water adsorbed on the acid sites is a direct function of temperature. High temperature will cause water to desorb from the acid site opening up the pathway for subsequent olefin dimerization reactions—i.e. formation of hydrocarbons greater than the desired $C_8$ olefins—while lower temperature will decrease this reaction.

Hydrocarbon flow through the alkylation reaction zone containing the catalyst is typically controlled to provide an olefin liquid hourly space velocity (LHSV) sufficient to convert about 99 percent by weight of the fresh olefin to alkylate product. In some embodiments, olefin LHSV values fall within the range of about 0.01 to about 10 $hr^{-1}$. Because the conversion of tertiary alcohol to olefin in the reactor is substantially quantitative, the olefin LHSV and the tertiary alcohol LHSV can be roughly the same.

The product composition of the olefin dimerization reaction described herein can be dependent on the reaction conditions. As will be shown in the examples, however, under the appropriate temperature, pressure, and solid acid catalyst, conversion of TBA to isobutene and subsequent conversion of isobutene to isooctene can be achieved at very high percentages. Moreover, the isooctene formed is highly selective for trimethylpentene over dimethylhexene. Additionally, of the trimethylpentene formed, a large proportion is 2,4,4-trimethyl-1-pentene as compared to 2,4,4-trimethyl-2-pentene. This is significant because trimethylpentene has a higher octane rating than dimethyhexene and 2,4,4-trimethyl-1-pentene is preferable to 2,4,4-trimethyl-2-pentene because terminal olefins are generally more active towards hydrogenation than internal olefins due to steric hindrance. The isooctene product can then be hydrogenated to form isooctane.

As discussed, this can correspond to an alkylate product having a higher octane value than would be obtained by a comparable process where isobutane and isobutene feeds are reacted using sulfuric acid as the catalyst. In some aspects, a naphtha boiling range portion of the alkylation effluent can have an octane rating, as determined based on (RON+MON)/2, of at least 95, or at least 98, or at least 100. In particular, in some aspects the naphtha boiling range portion of the alkylation effluent can have an octane rating of about 95 to about 100, or about 98 to about 102. Additionally, in aspects where oxygenate impurities are present in the initial feed to the alkylation reaction, a portion of those impurities can be present in the alkylation effluent. For example, acetone generated during selective oxidation of isobutane may not be fully converted under alkylation conditions. In aspects where acetone from a selective oxidation process is included as part of the feed to the alkylation reactor, unconverted acetone can correspond to 0.01 mol % to 0.5 mol % of the alkylation effluent on a dry basis, or 0.05 mol % to 0.5 mol %. Dry basis refers to the hydrocarbon portion of the alkylation effluent, which excludes any water present in the alkylation effluent.

Example Configurations

Figure 2A:
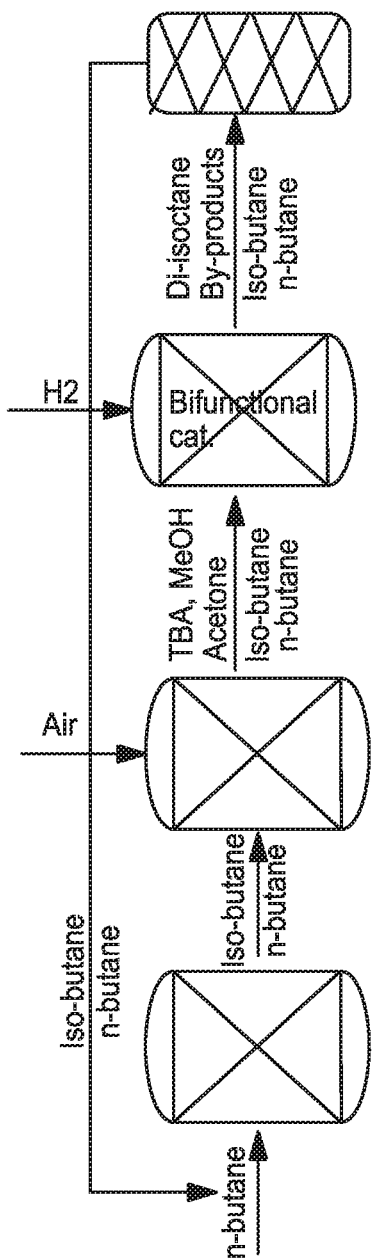
FIG. 2a schematically shows an example of a process configuration for producing alkylate from isoparaffins according to the present disclosure.
Figure 2B:
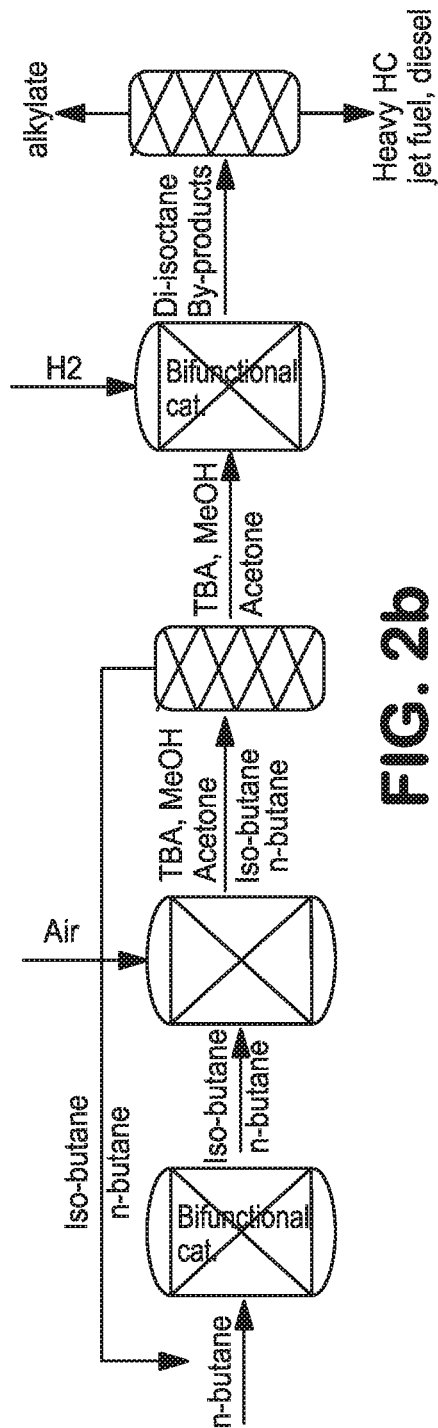
FIG. 2b schematically shows another example of a process configuration for producing alkylate from isoparaffins according to the present disclosure.

FIG. 2a shows an example of a reactor configuration for converting n-paraffins (such as butane) to alkylate. The figures are described with reference to butane and isobutane. It would be appreciated by a person of skill in the art other n-paraffin feeds could be used. In FIG. 2a, a feed including n-butane can be introduced into an isomerization reactor containing a bifunctional catalyst to convert the n-butane in the feed to isobutane. The feed containing isobutane and unreacted n-butane exits the isomerization reactor and enters an oxidation reactor. An oxygen-containing stream such as air, can also be introduced via an oxidant inlet. Isobutane is converted to tert-butanol ("TBA") via selective oxidation in the oxidation reactor. The oxidation effluent stream that includes unreacted isobutane, unreacted n-butane and TBA. The oxidation effluent stream can include additional oxygenates and/or other products formed during oxidation, such as methanol and/or acetone. The oxidation effluent stream (or at least a portion thereof) can then be introduced into dehydration/dimerization reactor via a reactor inlet. The dehydration/dimerization reactor can include a solid acid catalyst (such as an MWW framework catalyst, for example MCM-49). Within the dehydration/dimerization reactor TBA is dehydrated to form isobutene, which is then dimerized to form iso-octene. The dehydration and dimerization can occur in the same or different reactor vessel and is shown as the same vessel in FIG. 2a for simplicity. The dehydration/dimerization reactor can also include an inlet for a hydrogen-containing stream to hydrogenate the iso-octene to form iso-octane alkylate. Optionally, a separation stage can correspond to a distillation column to produce desired fractions from the effluent from the dehydration/dimerization reactor. In the example shown in FIG. 2a, the effluent is separated to form a water product, an iso-octane alkylate product, and an unreacted isoparaffin and n-paraffin stream that can optionally but preferably be recycled for use as part of the n-paraffin feed. Optionally, other side products in the alkylation effluent that boil below the naphtha boiling range can also be separated out (not shown). FIG. 2b shows an alternative system configuration wherein the separation stage comprising a distillation column is introduced after oxidation of the iso-butane to form TBA, but before introduction of the to the dehydration/dimerization reactor.

In the example configuration shown in FIG. 2a, the outlet of the oxidation reactor is shown as being in direct fluid communication with the inlet of the alkylation reactor. Direct fluid communication refers to fluid communication without passing through intervening reactor, separator, or other processing element that alters the composition of the effluent from the oxidation reactor. Fluid communication between reaction system elements that involves passing through one (or more) intervening processing elements can be referred to as indirect fluid communication.

EXAMPLE 1

Preparation of 80 wt % MCM-49/20 wt % Alumina Catalyst 80 parts MCM-49 zeolite crystals were combined with 20 parts pseudoboehmite alumina, on a calcined dry weight basis. The MCM-49 and pseudoboehmite alumina dry powder were placed in a muller or a mixer and mixed for about 10 to 30 minutes. Sufficient water and 0.05% polyvinyl alcohol were added to the MCM-49 and alumina during the mixing process to produce an extrudable paste. The extrudable paste was formed into a 1/20 inch quadralobe extrudate using an extruder. After extrusion, the 1/20th inch quadralobe extrudate was dried at a temperature ranging from 250° F. to 325° F. (121° C. to 163° C.). After drying, the dried extrudate was heated to 1000° F. (538° C.) under flowing nitrogen. The extrudate was then cooled to ambient temperature and humidified with saturated air or steam.

After humidification, the extrudate was ion exchanged with 0.5 to 1 N ammonium nitrate solution. The ammonium nitrate solution ion exchange was repeated. The ammonium nitrate exchanged extrudate was then washed with deionized water to remove residual nitrate prior to calcination in air. After washing the wet extrudate was dried. The exchanged and dried extrudate was then calcined in a nitrogen/air mixture to a temperature 1000° F. (538° C.).

EXAMPLE 2

Procedure for Dehydration

The reactor used in these experiments comprised a stainless steel tube having an internal diameter of 3/8 inches (~0.95 cm), a length of 20.5 inches (~52 cm) and a wall thickness of 0.035 inches (~0.089 cm). A piece of stainless steel tubing 8¾ inches (~22.2 cm) long×⅜ inches (~0.95 cm) external diameter and a piece of ¼ inch (~0.64 cm) tubing of similar length were positioned in the bottom of the reactor (one inside of the other) as a spacer to position and support the catalyst in the isothermal zone of the furnace. A ¼ inch (~0.64 cm) plug of glass wool was placed at the top of the spacer to keep the catalyst in place. A ⅛ inch (~0.32 cm) stainless steel thermo-well was placed in the catalyst bed, long enough to monitor temperature throughout the catalyst bed using a movable thermocouple. The catalyst was loaded with a spacer at the bottom to keep the catalyst bed in the center of the furnace's isothermal zone.

The catalyst was then loaded into the reactor from the top. The catalyst bed contained about 4.0 g of the MCM-49 catalyst of Example 1 sized to 14-25 mesh (700 to 1400 micron) and was 10 cm in length. A ¼ inch (~0.32 cm) plug of glass wool was placed at the top of the catalyst bed to separate quartz chips from the catalyst. The remaining void space at the top of the reactor was filled with quartz chips of similar size to the catalyst or larger (such as up to 14 mesh). The reactor was installed in the furnace with the catalyst bed in the middle of the furnace at the pre-marked isothermal zone. The reactor was then pressure and leak tested at 800 psig (~5.5 MPag).

500 cc ISCO syringe pumps were used to introduce the feed to the reactor. One ISCO pump was used for pumping an isobutane feed and a second ISCO pump was used to pump a blend of TBA (88 wt %), acetone (8 wt %), and methanol (4 wt %), hereinafter referred to as the TBA Blend. A Grove "Mity Mite" back pressure controller was used to control the reactor pressure at about 750 psig (~5.2 MPag). On-line GC analyses were taken to verify feed and the product composition. The feed (chemical grade isobutane and TBA or TBA Blend were used) was then pumped through the catalyst bed with the catalyst bed held at 150° C. The products exiting the reactor flowed through heated lines routed to GC then to three cold (5-7° C.) collection pots in series. The non-condensable gas products were routed through a gas pump for analyzing the gas effluent. Material balances were taken at 24 hr intervals. Samples were taken for analysis. The material balance and the gas samples were taken at the same time while an on-line GC analysis was conducted for doing material balance.

EXAMPLE 3

Alkylation Process with TBA

The system and procedures of Example 2 (including the catalyst of Example 1) were used to perform alkylation a feed corresponding to a 40:1 (vol/vol) mixture of isobutane and TBA. The alkylation reaction was conducted for 8 days at a temperature of about 150° C. and an initial LHSV of about 2.5 $hr^{-1}$.

EXAMPLE 4

Alkylation Process with TBA Blend

The system and procedures of Example 2 (including the catalyst of Example 1) were used to perform alkylation a feed corresponding to a 40:1 (vol/vol) mixture of isobutane and TBA Blend. The alkylation reaction was conducted for 8 days at a temperature of about 150° C. and an initial LHSV of about 2.5 $hr^{-1}$.

Figure 3:
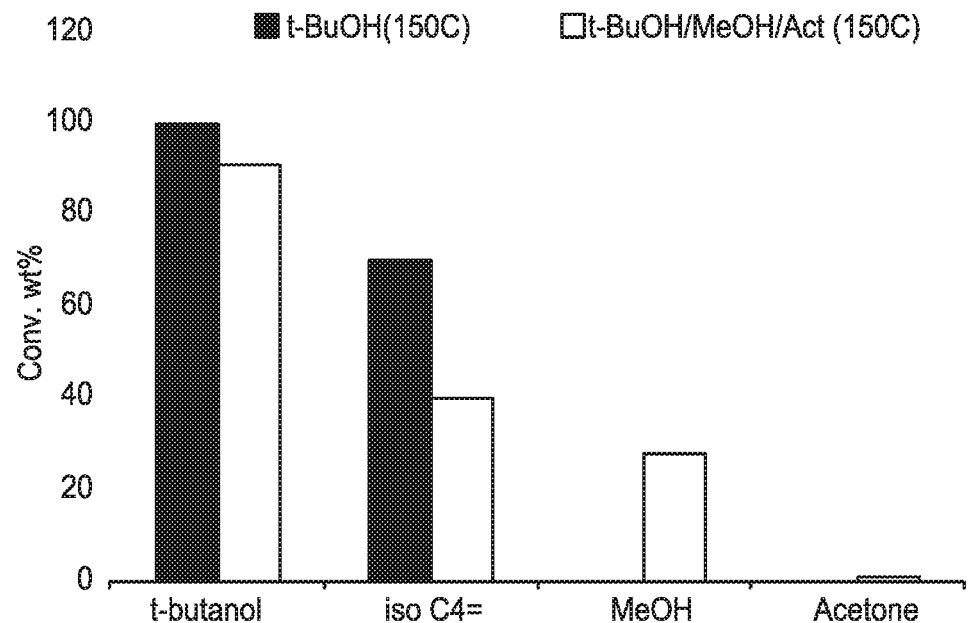
FIG. 3 shows results shows conversion rates of t-butanol, isobutene, methanol, and acetone as described in Examples 3 and 4.
Figure 4:
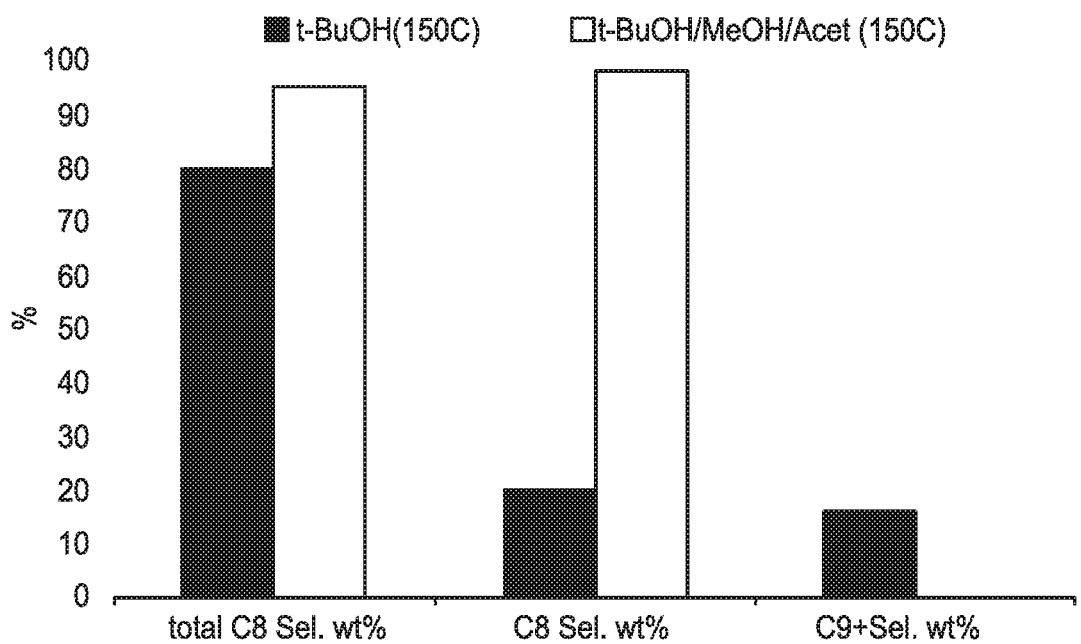
FIG. 4 shows results shows product selectivity resulting from the processes described in Examples 3 and 4.

FIG. 3 and FIG. 4 depict the activity and selectivity advantages of using an MWW framework type catalyst in the above-described processes. As shown in FIG. 3, 100% conversion of TBA is obtained on TBA and about 90% conversion of TBA in the TBA Blend is obtained. Of the isobutene formed in-situ from conversion of TBA, about 70% is converted in the TBA-only stream and about 40% is converted in the TBA-Blend stream. About 25% of methanol in the TBA Blend was converted. No acetone conversion was observed. MCM-49 catalyzes both in-situ TBA dehydration followed by dimerization.

As shown in FIG. 4, the presence of oxygenates in the feed promotes the formation of $C_8$ olefins as compared to the TBA-only feed. Indeed, nearly all (>98%) of all $C_8$ molecules formed using the TBA Blend were $C_8$ olefins. Moreover, the presence of oxygenates appears to have inhibited the undesirable formation $C_{9+}$ hydrocarbons. Without being bound by a particular theory, it is believed that the oxygenates may interact with the catalyst acid sites and moderate their activity towards olefin dimerization. Moreover, the process shows substantial advantage because it is able to be carried out a lower reaction temperature of about 150° C. to about 190° C., with the most preferred yields occurring at a reaction temperature of about 170° C.

This demonstrates that MWW framework catalysts can be suitable for performing both in-situ generation of isobutene (and/or other iso-olefins) while also remaining suitable for providing high rates of olefin conversion under alkylation conditions.

Additional Embodiments

Embodiment 1. A method for the production of high octane hydrocarbon, comprising: oxidizing an isobutane containing feed in the presence of oxygen to form an oxidation effluent comprising tert-butyl alcohol ("TBA") and an oxygenate impurity, at least 0.5 wt % of the isobutane in the isobutane containing feed being converted under the oxidation conditions; exposing at least a portion of the oxidation effluent to a solid acid catalyst, wherein the solid acid catalyst comprises a crystalline microporous material of the MWW framework type, under dehydration conditions to form a dehydration effluent comprising $C_4$ hydrocarbons; at least 80% of the TBA being converted under the dehydration conditions; exposing at least a portion of the dehydration effluent to a second solid acid catalyst, wherein the second solid acid catalyst comprises a crystalline microporous material of the MWW framework type, under dimerization conditions to form a dimerization effluent comprising $C_8$ hydrocarbons, wherein at least 90% of the $C_8$ hydrocarbons in the dimerization effluent are $C_8$ olefins.

Embodiment 2. The method of embodiment 1, further comprising hydrogenating the $C_8$ olefins.

Embodiment 3. The method of any of the previous embodiments, further comprising converting an n-butane containing feed to isobutane via isomerization over a bifunctional catalyst to form the isobutane containing feed.

Embodiment 4. The method of any of the previous embodiments, wherein the oxygenate impurity comprises water, methanol, acetone, or a combination thereof.

Embodiment 5. The method of any of the previous embodiments, wherein the oxygenate impurity comprises methanol and acetone.

Embodiment 6. The method of embodiment 3, further comprising: hydrogenating the $C_8$ olefins; and recycling a portion of unconverted n-butane, unconverted isobutane, or a combination of unconverted n-butane and unconverted isobutane to the n-butane containing feed.

Embodiment 7. The method of embodiment 6, wherein the recycling occurs after the hydrogenating.

Embodiment 8. The method of embodiment 6, wherein the recycling occurs after the oxidizing and before exposing at least a portion of the oxidation effluent to a solid acid catalyst under dehydration conditions.

Embodiment 9. The method of any of the previous embodiments, wherein the crystalline microporous material of the MWW framework type of either the first or second solid acid catalyst is selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and mixtures thereof.

Embodiment 10. The method of any of the previous embodiments, wherein the dimerization conditions include a dimerization temperature of about 100° C. to about 210° C., e.g. about 150° C. to about 190° C.

Embodiment 11. The method of any of the previous embodiments, wherein the dimerization conditions include a dimerization pressure of about 15 psig to about 1000 psig.

Embodiment 12. The method of any of the previous embodiments, wherein the oxidation effluent further comprises $C_{4+}$ isoparaffins and $C_{4+}$ n-paraffins.

Embodiment 13. The method of any of the previous embodiments, wherein the $C_8$ hydrocarbon portion of the dimerization effluent has an octane rating, as determined by (RON+MON)/2, of at least 95.

Embodiment 14. The method of any of the previous embodiments, wherein the solid acid catalyst comprises a mixed metal oxide based on oxides of Fe/W/Zr, W/Zr, Ce/W/Zr, Cu/W/Zr, Mn/W/Zr, or a combination thereof.

Embodiment 15. The method of any of the previous embodiments, wherein the solid acid catalyst further comprises an inorganic oxide binder.

Embodiment 16. The method of any of the previous embodiments, wherein the solid acid catalyst and the second solid acid catalyst are the same.

Embodiment 17. A system for the production of high octane hydrocarbon comprising: an oxidation reactor comprising an isoparaffin feed inlet and an oxidation reactor outlet; a dehydration reactor comprising a dehydration reactor inlet, a dehydration reactor outlet, and a solid acid catalyst comprising a zeolite, a mixed metal oxide, a crystalline microporous material of the MWW framework type, or a combination thereof, the dehydration reactor inlet being in fluid communication with the oxidation reactor outlet; a dimerization reactor comprising a dimerization reactor inlet, a dimerization reactor outlet, and a solid acid catalyst comprising a zeolite, a mixed metal oxide, a crystalline microporous material of the MWW framework type, or a combination thereof, the dimerization reactor inlet being in fluid communication with the dehydration reactor outlet; and a hydroprocessing reactor comprising a hydroprocessing reactor inlet, a hydroprocessing reactor outlet, and a hydroprocessing catalyst, the hydroprocessing reactor inlet being in fluid communication with the dimerization reactor outlet.

Embodiment 18. The system of embodiment 17, wherein the dehydration reactor, the dimerization reactor, and the hydroprocessing reactor are contained within a single vessel.

Embodiment 19. The system of any of embodiments 17 and 18, further comprising a recycle line providing fluid communication between the dimerization reactor outlet and the isoparaffin feed inlet.

Embodiment 20. The system of any of embodiments 17-19, further comprising: a distillation vessel interposed between the oxidation reactor and the dehydration reactor;

and a recycle line providing fluid communication between the distillation vessel and the isoparaffin feed inlet.

Embodiment 21. The system of any of embodiments 17-20, wherein the dimerization reactor and the hydroprocessing reactor are contained within a single vessel.

Embodiment 22. The system of any of embodiments 17-21, further comprising an isomerization reactor with an n-paraffin stream inlet and an isoparaffin feed outlet, wherein the isoparaffin feed outlet of the isomerization reactor is in fluid communication with the isoparaffin feed inlet of the oxidation reactor.

The present invention has been described above with reference to numerous embodiments and specific examples. Many variations will suggest themselves to those skilled in this art in light of the above detailed description. All such obvious variations are within the full intended scope of the appended claims.

The invention claimed is:

1. A method for the production of high octane hydrocarbon, comprising:
   oxidizing an isobutane containing feed in the presence of oxygen to form an oxidation effluent comprising tert-butyl alcohol ("TBA") and an oxygenate impurity wherein the oxygenate impurity comprises water, methanol, and acetone, wherein at least 0.5 wt % of the isobutane in the isobutane containing feed is converted under the oxidation conditions;
   directly exposing at least a portion of the oxidation effluent to a first solid acid catalyst, wherein the first solid acid catalyst comprises a crystalline microporous material of the MWW framework topology, under dehydration conditions to form a dehydration effluent comprising $C_4$ hydrocarbons; at least 80% of the TBA being converted under the dehydration conditions; and
   directly exposing at least a portion of the dehydration effluent to a second solid acid catalyst, wherein the second solid acid catalyst comprises a crystalline microporous material of the MWW framework topology, under dimerization conditions to form a dimerization effluent comprising $C_8$ hydrocarbons, wherein at least 90% of the $C_8$ hydrocarbons in the dimerization effluent are $C_8$ olefins.

2. The method of claim 1, further comprising hydrogenating the $C_8$ olefins.

3. The method of claim 1, further comprising converting an n-butane containing feed to isobutane via isomerization over a bifunctional catalyst to form the isobutane containing feed.

4. The method of claim 3, further comprising:
   hydrogenating the $C_8$ olefins; and
   recycling a portion of unconverted n-butane, unconverted isobutane, or a combination of unconverted n-butane and unconverted isobutane resulted from the isomerization and/or the oxidation to the n-butane containing feed.

5. The method of claim 4, wherein the recycling occurs after the hydrogenating.

6. The method of claim 4, wherein the recycling occurs after the oxidizing and before exposing at least a portion of the oxidation effluent to the first solid acid catalyst under the dehydration conditions.

7. The method of claim 1, wherein the crystalline microporous material of the MWW framework topology of either the first or second solid acid catalyst is selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and mixtures thereof.

8. The method of claim 1, wherein the crystalline microporous material of the MWW framework topology of either the first or second solid acid catalyst is any of MCM-22, MCM-36, MCM-49, and MCM56.

9. The method of claim 1, wherein the dimerization conditions include a dimerization temperature of about 100° C. to about 210° C.

10. The method of claim 1, wherein the dimerization conditions include a dimerization temperature of about 150° C. to about 190° C.

11. The method of claim 1, wherein the dimerization conditions include a dimerization pressure of about 15 psig to about 1000 psig.

12. The method of claim 1, wherein the oxidation effluent further comprises $C_{4+}$isoparaffins and $C_{4+}$n-paraffins.

13. The method of claim 1, wherein the $C_8$ hydrocarbons in the dimerization effluent have an octane rating, as determined by (RON +MON)/2, of at least 95.

14. The method of claim 1, wherein the first solid acid catalyst comprises a mixed metal oxide based on oxides of Fe/W/Zr, W/Zr, Ce/W/Zr, Cu/W/Zr, Mn/W/Zr, or a combination thereof.

15. The method of claim 1, wherein the first solid acid catalyst further comprises an inorganic oxide binder.

16. The method of claim 1, wherein the first solid acid catalyst and the second solid acid catalyst are the same.

* * * * *